United States Patent
Dooney, Jr.

(10) Patent No.: US 9,320,512 B2
(45) Date of Patent: Apr. 26, 2016

(54) SELF-CINCHING SOFT ANCHORS

(71) Applicant: Arthrex, Inc., Naples, FL (US)

(72) Inventor: Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 218 days.

(21) Appl. No.: 13/953,953

(22) Filed: Jul. 30, 2013

(65) Prior Publication Data

US 2014/0052178 A1 Feb. 20, 2014

Related U.S. Application Data

(60) Provisional application No. 61/684,426, filed on Aug. 17, 2012.

(51) Int. Cl.
*A61B 17/04* (2006.01)
*A61F 2/08* (2006.01)

(52) U.S. Cl.
CPC ........... *A61B 17/0401* (2013.01); *A61F 2/0811* (2013.01); *A61B 2017/042* (2013.01); *A61B 2017/0403* (2013.01); *A61B 2017/0409* (2013.01); *A61F 2002/0888* (2013.01)

(58) Field of Classification Search
CPC .................. A61B 17/0401; A61B 2017/0409; A61B 2017/0406; A61B 2017/0477; A61B 2017/0414; A61B 2017/0646; A61B 17/0642
USPC .................................................. 606/228, 232
See application file for complete search history.

(56) References Cited

U.S. PATENT DOCUMENTS

| | | | |
|---|---|---|---|
| 2008/0027446 A1* | 1/2008 | Stone et al. | 606/73 |
| 2008/0046009 A1* | 2/2008 | Albertorio et al. | 606/232 |
| 2011/0264141 A1* | 10/2011 | Denham et al. | 606/232 |
| 2012/0239085 A1* | 9/2012 | Schlotterback et al. | 606/228 |
| 2012/0290004 A1* | 11/2012 | Lombardo et al. | 606/232 |

FOREIGN PATENT DOCUMENTS

| | | |
|---|---|---|
| EP | 2 430 984 A1 | 3/2012 |
| EP | 2 572 650 A1 | 3/2013 |
| WO | WO 2013/074691 A1 | 5/2013 |

* cited by examiner

*Primary Examiner* — Katherine M Shi
(74) *Attorney, Agent, or Firm* — Blank Rome LLP

(57) ABSTRACT

Suture constructs and methods for soft tissue to bone repairs. The suture construct is a soft anchor which is self-cinching and has the ability to compress from a first, extended, uncompressed position to a second, folded or compressed position. The soft anchor may have a tubular/sleeve/sheath shape and may be formed essentially of a flexible, soft material such as suture, for example, a loosely braided UHMWPE sheath having a tubular configuration.

6 Claims, 2 Drawing Sheets

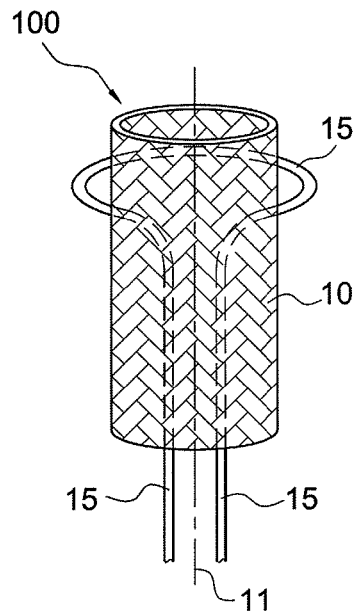
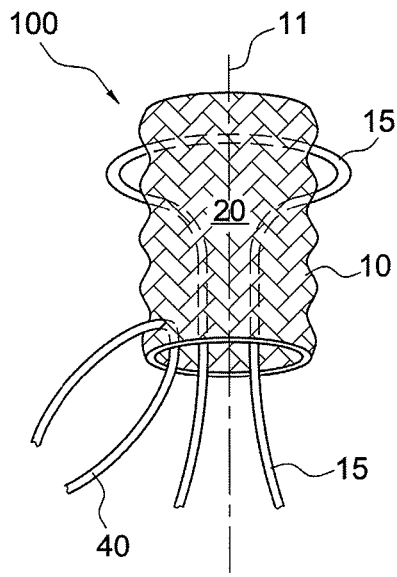
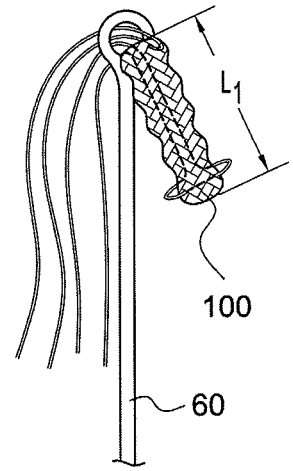
FIG. 1(a)  FIG. 1  FIG. 2
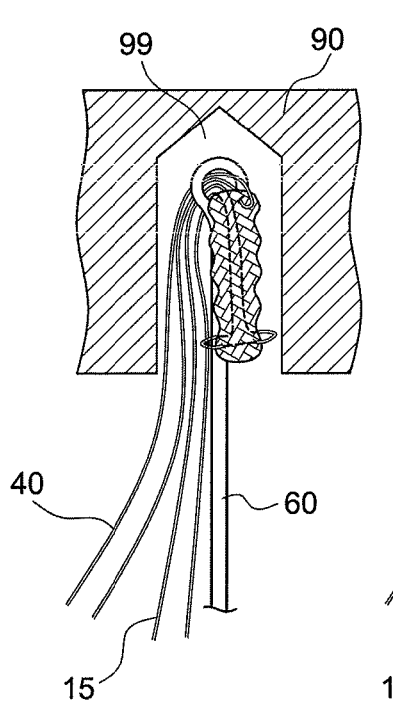
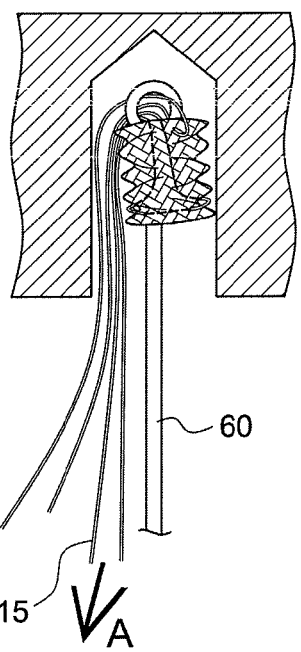
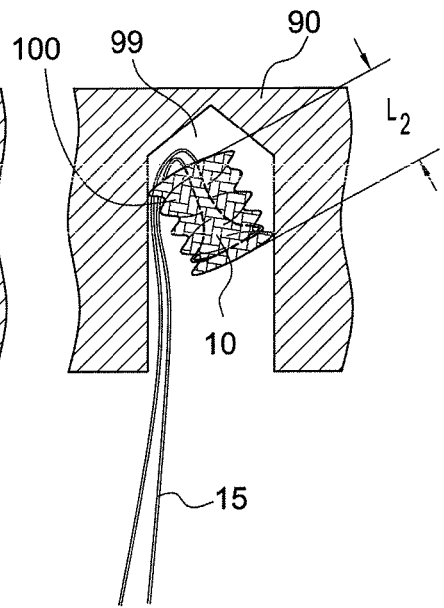
FIG. 3  FIG. 4  FIG. 5

SELF-CINCHING SOFT ANCHORS

CROSS-REFERENCE TO RELATED APPLICATIONS

This application claims the benefit of U.S. Provisional Application No. 61/684,426 filed Aug. 17, 2012, the disclosure of which is incorporated by reference in its entirety herein.

FIELD OF THE INVENTION

The present invention relates to surgical devices and, in particular, to soft suture-based anchors.

BACKGROUND OF THE INVENTION

Current soft suture anchors achieve fixation to bone by bunching up inside a drilled hole/socket in the bone. The soft suture anchor is inserted deep into the hole/socket and pulled back to bunch up. The friction between the soft suture anchor and the hole/socket bunches up the anchor when pulled back through the hole/socket.

It would be desirable to provide a suture construct that may be knotless and that is formed essentially of a soft material such as suture (or suture-based materials or other soft materials and/or compositions) with the ability to be inserted into a bone hole/socket at the desired level to be inserted within the hole/socket, without relying on pulling back the anchor through the drilled hole/socket. Also needed is a method of achieving increased final fixation of a soft suture anchor that bunches up within a drilled hole/socket.

SUMMARY OF THE INVENTION

The present invention provides soft anchors which are designed to be inserted into the bone but which have sliding, tying flexible strand(s) that slide freely through the body of the anchors. The sliding strand(s) also compress the body of the anchor to fixate it in the bone hole/socket at the desired level within the bone hole/socket. An additional flexible strand (such as suture) holds the construct to an inserter instrument to keep the construct at the bottom of the bone hole/socket.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 1 illustrates a front view of a soft, self-cinching suture-based anchor according to an exemplary embodiment of the present invention.

FIG. 1(a) is a perspective view of the soft, self-cinching suture-based anchor of FIG. 1.

FIG. 2 illustrates the soft, self-cinching suture-based anchor of FIG. 1 secured to a pusher/inserter instrument.

FIGS. 3-5 illustrate subsequent steps of a method of securing the soft, self-cinching suture-based anchor of FIG. 1 in bone.

DETAILED DESCRIPTION OF THE EMBODIMENTS

Figure 6:
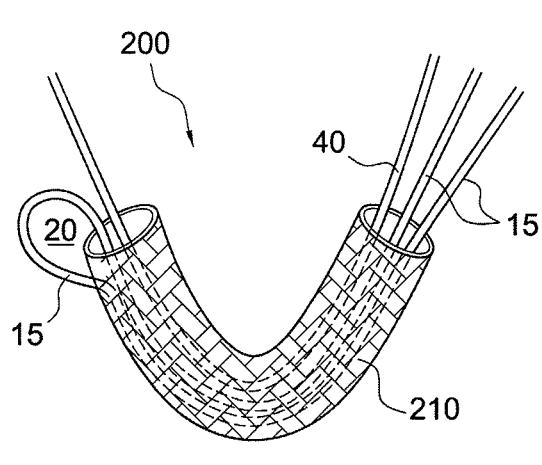
FIG. 6 illustrates a soft, self-cinching suture-based anchor according to another exemplary embodiment of the present invention.

The present invention provides surgical systems and methods for knotted or knotless soft tissue repair and fixation, such as fixation of soft tissue (ligament, tendon, graft, etc.) to bone.

The tissue repairs of the present invention include soft anchors formed of various soft materials and provided in various shapes and configurations that confer the anchors the ability to be easily inserted within bone tunnels/sockets/holes and be bunched up within the bone tunnels/sockets/holes. The soft anchors are formed essentially of soft materials such as yarns, fibers, filaments, strings, fibrils, strands, sutures, etc. or combinations of such soft materials. The soft materials may be synthetic or natural materials, or combinations of synthetic and natural materials.

The anchors may be in the form of any sleeve/sheath structure which may be provided with open or closed ends, or with at least one open end or with at least one closed end. The anchors may also have a tubular shape, partially tubular shape, or may be in the form of a hollow shape construct. The anchors may be woven or braided structures, or may be formed of yarns, fibers, or filaments or similar materials, or combinations of these materials. If the anchors are formed of suture, the suture and the anchors are typically without a core. In exemplary-only embodiments, the soft anchors are suture-based anchors formed essentially of suture.

The present invention also provides soft anchors (for example, soft suture-based anchors) which are designed to be inserted into the bone and which have sliding, tying suture(s) that slide freely through the body of the anchors. The sliding suture(s) also compress the body of the anchor to fixate it in the bone hole/socket at the desired level within the bone hole/socket. An additional suture may hold the construct to an inserter instrument to keep the construct at the bottom of the bone hole/socket.

According to an exemplary-only embodiment, the suture anchor of the present invention is a soft, suture-based anchor with a body that consists essentially of a flexible material such as suture, high-strength suture such as FiberWire® suture (disclosed in U.S. Pat. No. 6,716,234), suture tape such as FiberTape® (disclosed in U.S. Pat. No. 7,892,256), suture chain such as FiberChain® (disclosed in U.S. Pat. No. 7,803,173), among others, or combination of these materials. Preferably, the body of the suture-based anchor is a high-strength suture, such as an ultrahigh molecular weight polyethylene (UHMWPE) suture which is the preferred material as this material allows passing of additional sutures through the body of the anchor, and as detailed below. The body of the soft, suture-based anchor may be a loosely braided UHMWPE suture that can be compressed to fixate in a bone hole/socket.

At least one additional suture may be added through the soft anchor (passed through the body of the soft suture anchor) so that they can freely slide to tie knot(s) and/or allow fixation of the suture anchor to a pusher/inserter instrument. The additional suture(s) also compress the body of the anchor for fixation into the bone hole/socket and aid in maintaining the soft anchor at the bottom of the hole/socket.

Referring now to the drawings, where like elements are designated by like reference numerals, FIGS. 1-10 illustrate exemplary soft, self-cinching anchors 100, 200 of the present invention that are formed essentially of a soft material. For simplicity, the embodiments described below will be detailed with reference to soft anchors 100, 200 as being exemplary suture-based anchors. However, the invention is not limited to these exemplary-only embodiments and contemplates soft anchors formed of any soft materials or combinations of such soft materials, and as desired.

The self-cinching soft anchors 100, 200 may be in the form of a sheath, tube or sleeve or any similar structure. The self-cinching soft anchors 100, 200 may be also in the form of suture (for example, a UHMWPE sheath or a FiberWire® suture) or suture chain (such as FiberChain®) or suture tape (such as FiberTape®).

FIGS. 1-5 illustrate soft, suture-based anchor 100 formed essentially of a flexible, soft material 10 (for example, a loosely braided UHMWPE sheath or sleeve 10 or a similar structure having a tubular configuration) and a flexible strand 15 (soft independent suture 15) attached to (threaded through) the flexible material 10. FIGS. 6-10 illustrate soft, suture-based anchor 200 formed essentially of a flexible material 210 (for example, a loosely braided UHMWPE sheath or sleeve 210, or a similar structure having a tubular configuration) and a flexible strand 15 (soft independent suture 15) attached to (threaded through) the flexible material 210.

FIGS. 1-5 illustrate suture-based anchor 100 formed essentially of a flexible material 10 in an exemplary form of a loosely braided UHMWPE sheath or sleeve 10, or similar tubular structure. Flexible material 10 may be also a braided suture or a similar structure that can be compressed together to fixate in a bone hole, i.e., bunched up to achieve a final, compressed length which is smaller than the initial, uncompressed length.

Another flexible strand 15 (for example, a second suture which can be a FiberWire® or TigerWire® suture 15) is passed through the length of the flexible material 10 (with a needle, for example) in a suture-through-suture technique, as shown in FIGS. 1 and 1(a). Flexible strand 15 (second suture) passes through braided UHMWPE sheath 10 (soft material or first suture) and can slide to tie a knot. Flexible strand 15 also compresses the sheath 10 (soft material or first braided suture) to achieve an overall final length (compressed length) which is smaller than the initial, non-compressed length, for fixation in bone hole/socket.

The flexible strand 15 (for example, FiberWire® or TigerWire® suture 15) may circle back to exit through the exemplary UHMWPE sheath 10 near the spot where it entered, creating a loop/eyelet 20 within the body of the anchor.

The flexible strand 15 (FiberWire® or TigerWire® suture 15) may be passed through the material 10 (flexible strand 10) at different locations and as desired, for example, at predetermined insertion points on the length of the flexible strand 10. The end of the FiberWire® or TigerWire® suture 15 may be brought back to reenter the UHMWPE sheath 10 near the spot where it first entered (or in its vicinity) to form loop 20. Preferably, the flexible strand 15 is threaded through about the whole length of the sheath 10. Flexible strand 15 may be passed through soft material 10 in at least two different directions, for example, in both transversal and longitudinal directions relative to longitudinal axis 11 of the flexible material 10 (tubular sleeve 10), and as shown in FIGS. 1 and 1(a).

FIG. 1 illustrates anchor 100 with at least one additional flexible strand 40 (for example, a third suture 40 for handling the construct with the inserter) passing through at least a portion of the flexible material 10, to hold the construct to inserter 60 (pusher instrument 60), as shown in FIG. 2. The inserter 60 may be any instrument that allows the anchor 100 to be inserted into a bone tunnel/socket/hole. As detailed below, when the soft, suture-based anchor 100 is inserted into a bone socket/tunnel employing the pusher instrument, the body of the anchor 100 may bunch up within the bone socket/tunnel. However, the sliding sutures 15 remain free to slide and untangled, to allow completion of the soft tissue repair, for example, to tie a knot to complete the soft tissue attachment to bone.

FIGS. 3-5 illustrate the insertion of soft, self-cinching suture-based anchor 100 into drilled hole 99 formed within bone 90. In FIG. 4, as the flexible strand 15 is pulled away from the drilled hole/socket 99 in the direction of arrow A, the braided sheath 10 compresses and bunches up inside the hole 99. In FIG. 5, the inserter 60 and the additional suture 40 (handling suture 40) are removed, with the ends of the flexible strand 15 remaining free to slide to tie a knot and to complete the soft tissue repair to bone. By being inserted, compressed and bunched up inside the hole 99, the length of the anchor 100 decreases from a first, initial, non-compressed length $L_1$ (FIG. 2) to a second, final, compressed length $L_2$ (FIG. 5) which is smaller than $L_1$, i.e., about half of $L_1$.

FIG. 6 illustrates another embodiment of a soft, self-cinching anchor of the present invention. Soft, self-cinching anchor 200 is similar to the soft anchor 100 in that it is also a suture-based anchor, i.e., it also contains flexible material/strand 210 formed essentially of a soft material such as suture (for example, a loosely braided UHMWPE braid) and an independent suture 15 (second flexible strand) attached to (threaded through) the flexible material/strand 210. The flexible material 210 has also a tubular configuration like the configuration of the sheath 10 of FIG. 1, but with an overall bent outer configuration.

Like in the previously-described embodiment, the flexible strand 15 (which may be a FiberWire® or TigerWire® suture, for example) may be passed through the material/suture 210 at different locations and as desired, for example, at predetermined insertion points on the length of the flexible material 210. The end of the FiberWire® or TigerWire® suture 15 may be brought back to reenter the UHMWPE sheath 210 near the spot where it first entered (or in its vicinity) to form loop 20. Preferably, the flexible strand 15 is threaded through about the whole length of the sheath 210. An additional flexible strand 40 (for example, a third suture 40 for handling the construct with an inserter) passes through at least a portion of the flexible material/strand 210, to hold the construct to inserter 260 (pusher instrument 260), as shown in FIG. 7.

Figure 7:
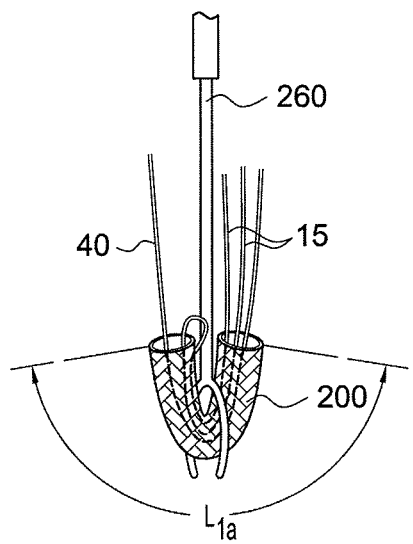
FIG. 7 illustrates the soft, self-cinching suture-based anchor of FIG. 6 secured to a pusher/inserter instrument.

FIG. 7 illustrates the construct 200 attached to inserter 260 (pusher instrument 260) which may be an instrument provided with a forked tip. As detailed below, when the soft, suture-based anchor 200 is inserted into a bone socket/tunnel employing the pusher instrument, the body of the anchor 200 may bunch up within the bone socket/tunnel. However, the sutures 15, 40 remain free to slide and untangled, to allow completion of the soft tissue repair, for example, to tie a knot to complete the soft tissue attachment to the bone.

Figure 8:
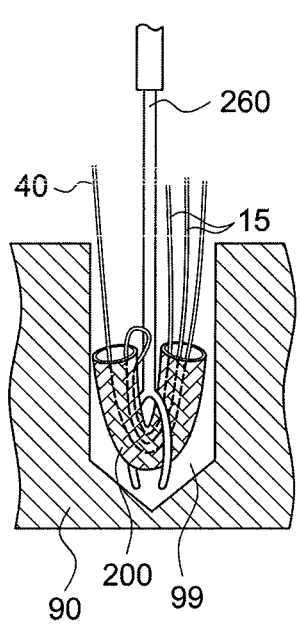
FIGS. 8-10 illustrate subsequent steps of a method of securing the soft, self-cinching suture-based anchor of FIG. 6 in bone.
Figure 9:
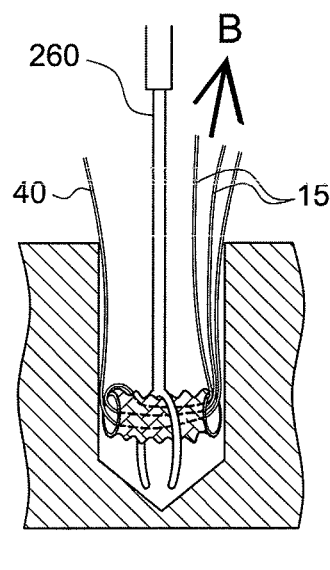
Figure 10:
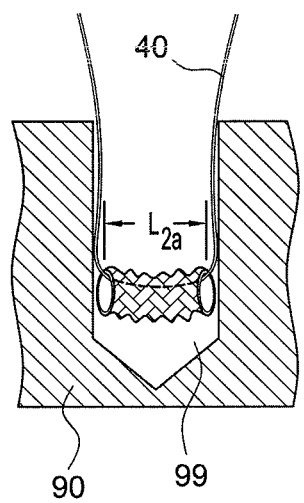

FIGS. 8-10 illustrate the insertion of soft, self-cinching suture-based anchor 200 into drilled hole 99 formed within bone 90. In FIG. 9, as the flexible strand 15 is pulled away from the drilled hole/socket 99 in the direction of arrow B, the braided sheath 210 compresses and bunches up inside the hole 99. In FIG. 10, the inserter 260 and the flexible strand 15 (second suture) are removed, with the ends of the additional suture 40 (handling suture 40) remaining free to slide to tie a knot and to complete the soft tissue repair to bone. Strand 15 may be also left in place as a second sliding suture for tissue repair. The overall length of the soft anchor 200 also decreases from the initial, non-compressed length $L_{1a}$ (FIG.

7) to a final, compressed length $L_{2a}$ (FIG. 10) which is smaller than $L_{1a}$, for example, about half of $L_{1a}$.

The materials employed for the formation of the soft anchors 100, 200 may be loosely braided ultrahigh molecular weight polyethylene (UHMWPE) sutures, which may be braided with at least one other fiber, natural or synthetic, to form lengths of suture material. The suture-based anchors 100, 200 may be also formed of suture tape such as FiberTape® as disclosed in U.S. Pat. No. 7,892,256, the disclosure of which is incorporated by reference in its entirety herewith. The suture tapes may have the same, uniform width or may have different widths, and may comprise the same or different materials.

The flexible, soft material forming the soft anchors 100, 200 may be also formed of suture tape or a combination of suture and tape, a stiff material, or combination of stiff and flexible materials, depending on the intended application. Alternatively, the flexible material may be formed in the shape of a folding tube suture anchor which may contain textile or homogenous material. The folding tube anchor may be formed of a tube (cylinder or sleeve) provided with apertures/holes to allow the flexible strand 15, 40 to pass therethrough. When the tube is inserted into a bone tunnel/socket and when tension is applied, the tube folds and lodges into the bone tunnel/socket but the tying, sliding sutures remain free for additional manipulation and surgical procedures.

As noted above, the soft anchors 100, 200 may be formed of any soft materials such as yarns, fibers, filaments, strings, fibrils, strands, sutures, etc. or combinations of such soft materials. The soft materials may be woven, braided, knitted or otherwise interlocked with each other to achieve the soft anchors of the present invention. The soft materials may be synthetic or natural materials, or combinations of synthetic and natural materials. The anchors 100, 200 may be in the form of any sleeve/sheath/tubular structure which may be provided with open or closed ends, or with at least one open end or with at least one closed end. The anchors 100, 200 may also have a tubular or cylindrical shape, partially tubular shape, a sleeve-like shape, or may be in the form of any hollow or partially hollow shape construct provided with a cannulation extending at least along a portion of the length of the structure. The anchors 100, 200 may be woven or braided structures, or may be formed of yarns, fibers or similar materials, or combinations of these materials, that are joined/interlocked together by any known method in the art. In the exemplary-only embodiments above, the soft anchors 100, 200 of the present invention are suture-based anchors formed essentially of suture such as UHMWPE.

The soft anchors 100, 200 detailed above may be also employed with a self cinching suture mechanism that could be incorporated into the implant/anchor. Once the anchor is deployed, the surgeon would simply pull on the self-cinching suture strands to firmly secure the device and compress the tissue (for example, the rotator cuff). The soft anchors 100, 200 could be utilized for multiple additional indications such as, for example, AC joint reconstruction, syndesmosis reconstruction, quad/patellar tendon rupture repair, hallux-valgus repair, and any other tendon repair to bone.

The soft anchors 100, 200 detailed above may be also employed in conjunction with additional various knotted and/or knotless fixation devices (or combination of such knotted and knotless fixation devices), such as PushLock® anchors and/or SwiveLock® anchors to secure, for example, a medial row on rotator cuff repairs.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all falling within the scope of the invention. Accordingly, the invention is to be limited not by the specific disclosure herein, but only by the appended claims.

What is claimed is:

1. An anchor for surgical repairs consisting essentially of:
   a tubular sleeve formed of flexible material, the tubular sleeve being adapted to be compressed from a first, non-compressed position to a second, compressed position, the tubular sleeve having a first length, a cannulation, and two open ends;
   a flexible strand attached to the tubular sleeve, the flexible strand extending along the first length of the tubular sleeve and with ends exiting a same open end of the tubular sleeve so that, when the ends of the flexible strand are pulled, the tubular sleeve bunches up and achieves a second length which is smaller than the first length, and wherein the flexible strand is attached to one of the two open ends of the tubular sleeve by passing one end of the flexible strand through different points spaced apart a length of the tubular sleeve beginning with a first point at the one of the two open ends, and then passing the flexible strand around the tubular sleeve and circling back the other end of the flexible strand at a position adjacent the first point at the one of the two open ends, to reenter the tubular sleeve near the first point where the flexible strand first entered and to form a loop within the tubular sleeve at the one of the two open ends, and wherein the flexible strand is a sliding suture which freely slides within the tubular sleeve even when the tubular sleeve bunches up within a bone tunnel or socket; and
   another flexible strand attached to another of the two open ends of the tubular sleeve for allowing the tubular sleeve to be handled with an inserter.

2. The anchor of claim 1, wherein the flexible strand, when pulled, is designed to compress the tubular sleeve from the first, non-compressed position to the second, compressed position.

3. The anchor of claim 1, wherein, when the two ends of the flexible strand are pulled, the loop collapses and compresses the tubular sleeve from the first, non-compressed position to the second, compressed position.

4. The anchor of claim 1, wherein the flexible material is a suture, suture tape or suture chain.

5. The anchor of claim 1, wherein the flexible material is a braided sheath formed of ultrahigh molecular weight polyethylene.

6. The anchor of claim 1, wherein the flexible strand is a suture.

* * * * *